United States Patent [19]
Lennon et al.

[11] Patent Number: 5,945,082
[45] Date of Patent: *Aug. 31, 1999

[54] CYANOPHOSPHORUS COMPOUNDS AND THEIR PREPARATION

[75] Inventors: Patrick J. Lennon, Webster Grove; Sergey G. Vulfson, Chesterfield, both of Mo.

[73] Assignee: Monsanto Company, St. Louis, Mo.

[*] Notice: This patent is subject to a terminal disclaimer.

[21] Appl. No.: 08/996,946

[22] Filed: Dec. 23, 1997

Related U.S. Application Data

[60] Provisional application No. 60/034,514, Dec. 30, 1996.

[51] Int. Cl.$^6$ .................................. C07F 9/38; C07F 9/30
[52] U.S. Cl. .................. 423/302; 564/281; 564/291; 564/292; 568/9; 568/18; 568/27
[58] Field of Search .................. 423/302; 564/281, 564/291, 292; 568/9, 18, 27

[56] References Cited

U.S. PATENT DOCUMENTS

| | | |
|---|---|---|
| 2,402,703 | 6/1946 | Woodstock . |
| 2,702,299 | 2/1955 | Harris . |
| 3,432,277 | 3/1969 | Roesky ........................ 23/357 |
| 3,812,221 | 5/1974 | Braden et al. ............... 260/968 |
| 4,221,583 | 9/1980 | Gaertner et al. . |
| 4,568,432 | 2/1986 | Rogers . |

FOREIGN PATENT DOCUMENTS

| | | | |
|---|---|---|---|
| 300 936 | 9/1992 | Germany | ..................... C07F 9/40 |
| 96/15135 | 5/1996 | WIPO . | |

OTHER PUBLICATIONS

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem.* 552: 132–146 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc.* 117:7285–7286 (1995).

Shioiri et al., "Reaction of Diethyl Phosphorocyanidate(DEPC) with Carboxylic Acids. A New Synthesis of Carboxylic Esters and Amides," *Tetrahedron* 32(18):2211–2217 (1976).

Tung et al., "A New Method for the Preparation of O,O'–Dialkylphosphoryl Cyanides," *Hua Hsueh Hsueh Pao (Acta Chimica Sinica)* 31(3): 199–202 (1965).

Abstract—Database WPI, Section Ch, Week 7615, Derwent Publications Ltd., London, GB; Class B04, AN 76–27192X, XP002061354 & JP 51 023 225 A (Nippon Chem. Ind. Co. Ltd.), Feb. 24 1976.

Blanchard, J. "Préparation d–acides beta–amino–ethyl–phosphoniques" Tetrahedron,m; vol. 32, No. 4, 1976, Oxford GB, pp. 455–459, XP002061374.

Chemical Abstracts, vol. 093, No. 12, Sep. 22, 1980, Columbus, Ohio, US; abstract No. 123612, Zhurba, Y.I. et al., "Increase in the stability of silver complexes in the process of simultaneous developing and fixing" and ZH Nauchn, Pirkl. Fotogr. Kinematogr. (ZNPFAG, 00444561); 80; vol. 25(3); pp. 182–5, VSES. GOS Nauchno–Issled. Proektn. Inst. Khim.–Fotogr. Prom., Moscow; USSR; XP002061352.

Dyatkina, N. et al. Synthesis and antiviral activity of some fluorinated nucleotide derivativers: Nucleosides Nucleotides (NUNUD5, 07328311); 94; col. 13 (1–3); pp. 325–337; Engelhardt Inst. Mol. Biol.; Moscow; 117984, Russia XP002061348.

Kashemirov, B.A. "(E)–(Hydroxyimino)(hydroxymethoxyphosphinyl)acetic acid: Synthesis and pH dependent fragmentation," *Tetrahedron Letters,* vol. 36, No. 52, 1995, Oxford GB, pp. 9437–9440; XP002061351.

*Primary Examiner*—Michael G. Ambrose
*Attorney, Agent, or Firm*—Arnold, White & Durkee

[57] ABSTRACT

Novel cyanophosphorus compounds are disclosed. The preparation, purification, and characterization of dicyanophosphinate, cyanopolyphosphates, tricyanocyclotriphosphonate and tetracyanocyclotetraphosphate are presented.

49 Claims, No Drawings

CYANOPHOSPHORUS COMPOUNDS AND THEIR PREPARATION

This application claims the benefit of provisional application Ser. No. 60/034,514, filed Dec. 30, 1996.

BACKGROUND OF THE INVENTION

Organophosphorus compounds have numerous and varied applications, for example, in herbicides, insecticides, fertilizers, flame retardants and plasticizers and as precursors for the synthesis of other organophosphorus compounds. Cyanophosphonates and their derivatives are of particular interest due to their versatility in synthetic pathways and a wide range of chemistries can extend from both the phosphorus and cyano moieties.

A process for preparing dicyanophosphinate was described by Albrecht et al., Z. anorg. allg. Chem. 552:132–146 (1987), involving a reaction of triethylphosphite, carbon tetrachloride, trimethylammonium iodide and potassium cyanide in an acetonitrile solvent. The Albrecht process was reported to produce a complex mixture of phosphorus products, including dicyanophosphinate in a 2% yield. The products of the Albrecht process were identified by $^{31}$P NMR, with structures being determined from chemical shifts and P-H coupling constants on a 36.44 MHz NMR instrument. No purification of products of the Albrecht process was reported. Nevertheless, the inventors of the present invention have preliminary findings that indicate the Albrecht et al. process does not actually enable the production of a dicyanophosphinate product.

There exists a need for novel cyanophosphorus compounds and methods for their preparation to enable the preparation of organophosphorus materials with a variety of beneficial uses.

SUMMARY OF THE INVENTION

The invention relates to novel cyanophosphorus compounds and their preparation. The novel cyanophosphorus compounds of the present invention include dicyanophosphinate salts of the formula (I):

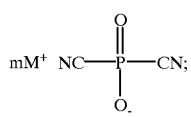
(I)

dicyanopolyphosphates of the formula (II):

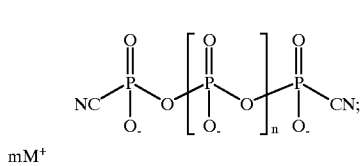
(II)

cyanopolyphosphates of the formula (III):

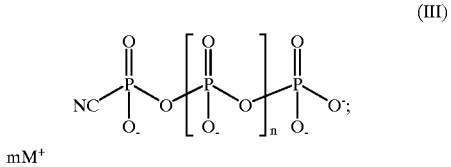
(III)

and polycyanocyclopolyphosphonate compounds of the formula (IV) and (V):

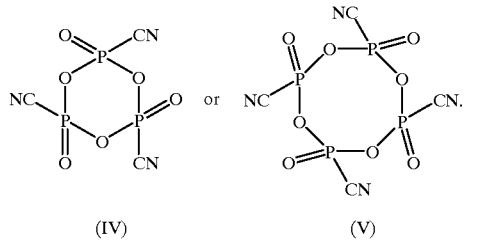
(IV)        (V)

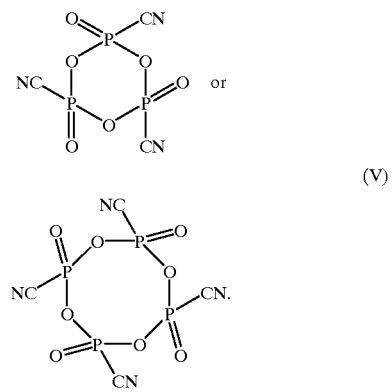
(IV)

(V)

In a preferred embodiment, these novel cyanophosphorus compounds are prepared by contacting phosphoric anhydride and a cyanide, preferably in the presence of a Lewis base, in a reaction mixture under sufficient conditions to produce one or more cyanophosphorus compounds of the formula I, II, III, IV and V. Synthesis details, purification strategies and molecular characterizations are presented for the novel compounds.

DESCRIPTION OF ILLUSTRATIVE EMBODIMENTS

The novel cyanophosphorus compounds of the present invention include dicyanophosphinate salts of the formula (I):

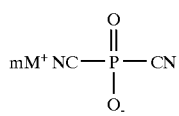
(I)

wherein M$^+$ comprises a suitable monovalent or polyvalent cation and m is a number, preferably an integer, indicating the number of M$^+$ cations for neutralization of the formula (I) compound.

The invention is also directed to novel dicyanopolyphosphates of the formula (II):

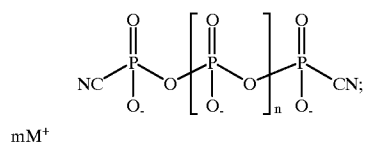

(II)

wherein $M^+$ comprises a suitable monovalent or polyvalent cation, m is a number, preferably an integer, indicating the number of $M^+$ cations for neutralization of the formula (II) compound and n is an integer.

The invention is further directed to novel cyanopolyphosphates of the formula (III):

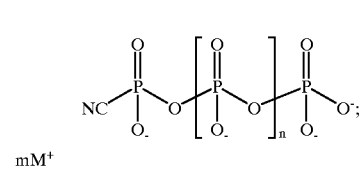

(III)

wherein $M^+$ comprises a suitable monovalent or polyvalent cation, m is a number, preferably an integer, indicating the number of $M^+$ cations for neutralization of the formula (III) compound and n is an integer.

The invention is further directed to novel polycyanocyclopolyphosphonate compounds of the general formula:

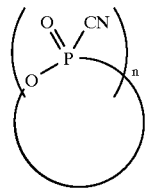

wherein n is 3 to 8. More preferably, the polycyanocyclopolyphosphonate compound is of the formula (IV) or (V):

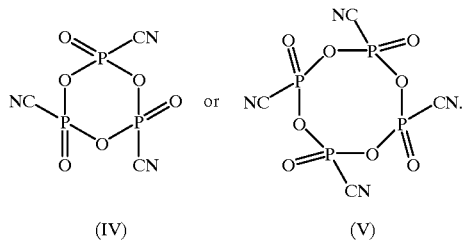

(IV)        (V)

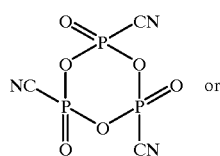

(IV)

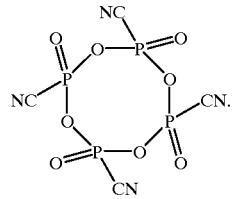

(V)

The compounds described above can be prepared by a process that involves a step of contacting phosphoric anhydride ($P_4O_{10}$) and a cyanide, preferably in the presence of a Lewis base, in a reaction mixture under sufficient conditions to produce at least one compound of the formula I, II, III, IV or V.

In a preferred embodiment, the process of the present invention involves charging a reaction vessel with a phosphoric anhydride, optionally with a nonreactive, polar solvent. A Lewis base is then added, preferably in an amount ranging from about 1 to about 10 molar equivalents relative to phosphoric anhydride, more preferably from about 2 to about 8 molar equivalents, and most preferably from about 3 to about 6 molar equivalents. That mixture is then heated under suitable conditions to dissolve or partially dissolve the phosphoric anhydride, e.g., preferably at a temperature of about 40° C. and for about 10 minutes. Subsequently a cyanide compound is added, preferably in an amount ranging from 1 to 15 molar equivalents relative to phosphoric anhydride, more preferably from about 2 to about 10 molar equivalents and most preferably from about 3.5 to about 8.5 molar equivalents. This mixture is then heated under suitable conditions to carry out the reaction. The reaction temperature is preferably between −20° C. and 150° C., and more preferably between 30° C. to 90° C. The reaction time preferably ranges from about 0.1 to about 50 hours, more preferably from about 0.5 to about 20 hours and most preferably from about 1 to about 6 hours. The Lewis base and any solvent can subsequently be removed from the product mixture, for example, under reduced pressure.

Phosphoric anhydride is commercially available, for example, from Aldrich Chemical Co. in assays in excess of 99.99%. The phosphoric anhydride is generally available in the form of a powder and can be added to the reaction mixture in various forms. For example, phosphoric anhydride can be added directly as a powder or as a slurry in a solvent or cosolvent.

The cyanide compound can be hydrogen cyanide or a cyanide salt that is sufficiently reactive with phosphoric anhydride to produce a cyanophosphorus compound of formula I, II, III, IV or V. For example, the cyanide compound can be an alkali metal cyanide, an alkaline earth metal cyanide, an ammonium cyanide, a tetraallyl ammonium cyanide, a tetraalkyl phosphonium cyanide, a tetraaryl phosphonium cyanide, a trialkyl sulfonium cyanide, a cyanide of a cationic form of an organic amine or mixtures thereof. The cyanide compound is preferably hydrogen cyanide, calcium cyanide, potassium cyanide, sodium cyanide, lithium cyanide, silver cyanide, gold cyanide, copper cyanide, tetrabutylammonium cyanide or mixtures thereof. More preferably, the cyanide compound is hydrogen cyanide, potassium cyanide, sodium cyanide, tetrabutylammonium cyanide or mixtures thereof.

The Lewis base is generally any base suitable for promoting the production of the cyanophosphorus compounds according to the invention. In a preferred embodiment, the Lewis base is triethylamine, diglyme, 4-isopropylpyridine, 4-dimethylaminopyridine, tris[2-(2-methoxyethoxy)ethyl] amine, 4-tert-butylpyridine, 4-(5-nonyl)-pyridine, trimethylamine, 1,8-bis(dimethylamino)naphthalene, 4-ethylpyridine, phenanthroline, piperidine, N,N,N',N'-tetramethyl ethylenediamine, 1,4,7,10,13-pentamethyl-1,4,7,10,13-pentaazacyclopentadecane, quinuclidine, N-methylpyrrolidine, 1,4-4diazobicyclo[2.2.2]-octane, 1-butylimidazole, 3-benzylpyridine, 1,5-pentamethylenetetrazole, tris[2(2-methoxyethoxy)ethyl] amine, N,N-dimethylaniline, collidine, N-benzylidine aniline, triphenylphosphine or mixtures thereof. More preferably, the Lewis base is 4-tert-butylpyridine, 4-(5-nonyl)pyridine, quinuclidine or N-methylpyrrolidine. The Lewis base can be added to the reaction mixture in an amount ranging from about 1 to about 10 molar equivalents, more preferably from 2 to about 8 molar equivalents and most preferably from 3 to about 6 molar equivalents relative to phosphoric anhydride.

The solvent can be any material that enhances the solubility of the reactants or promotes the formation of the desired products. Preferably the solvent is a polar aprotic solvent, for example, a nitrile such as acetonitrile, benzylcyanide, adiponitrile, propionitrile, dimethylacetonitrile, sulfolane or mixtures thereof More preferably, the solvent is acetonitrile, benzylcyanide or adiponitrile.

Further details and examples regarding the synthesis of cyanophosphonate derivatives from phosphoric anhydride and cyanide are provided in co-pending U.S. patent application Ser. No. 08/996,949, entitled "Method for Preparing Cyanophosphonate Derivatives from Phosphoric Anhydride and Cyanide," by Patrick J. Lennon and Sergey G. Vulfson filed Dec. 23, 1997.

The cation(s) acting as the counterion(s) in the cyanophosphorus compounds of the formula I, II and III are generally one or more monovalent or polyvalent cations suitable for the preparation of cyanophosphorus compounds according to the invention. In a preferred embodiment, the cation comprises a hydrogen cation, an alkali metal cation, an alkaline earth metal cation, a transition metal cation, a group III metal cation, a lanthanide cation, an actinide cation, a cationic form of a primary amine, a cationic form of a secondary amine, a cationic form of a tertiary amine, a cationic form of a polyamine, a cationic form of an amino acid, a cationic form of a dendrimeric amine, a cationic form of a heterocycle, an ammonium cation, a quarternary ammonium cation, a cationic hydrazine derivative, an amidinium cation, a sulfoxonium cation, a sulfonium cation, a phosphonium cation, a phosphazenium cation, a guanidinium cation or a cationic form of a biologically active amine. These cations can include any suitable anionic component, provided that they possess an overall positive charge.

The alkali metal cation, for example, is preferably a lithium, sodium, or potassium cation. The alkaline earth metal cation is preferably a calcium or magnesium cation. The transition metal cation is preferably a cationic form of titanium, zirconium, chromium, manganese, iron, cobalt, nickel, ruthenium, osmium, rhodium, iridium, palladium, platinum, molybdenum, copper, silver, gold, zinc or cadmium. The group III metal cation is preferably a cationic form of aluminum, gallium or indium. The lanthanide cation is preferably a cationic form of lanthanum, cerium, praseodymium, neodymium, samarium, europium, gadolinium, terbium, dysprosium, holmium, erbium, thulium, ytterbium or lutetium. The actinide cation is preferably a cationic form of thorium or uranium.

The primary amine cation is preferably a cationic form of a straight chain alkyl amine, a branched chain alkyl amine, an aminoalcohol derivative, an arylamine, an arylalkylamine, a cycloalkyl amine, a polycycloalkyl amine or mixtures thereof. The straight chain alkyl amine cation is preferably a cationic form of methylamine, ethylamine, 1-propylamine, 1-butylamine, 1-pentylamine, 1-hexylamine, 1-heptylamine, 1-octylamine, 1-decylamine, 1-dodecylamine, 1-tetradecylamine or 1-hexadecylamine. The cationic form of branched chain alkyl amine is preferably a cationic form of 2-aminopropane, 2-aminobutane, 2-methyl-2-aminopropane, 2-methyl-1-aminopropane, 2-aminopentane, 3-aminopentane, 3-methyl-1-aminobutane, 2,2-dimethylaminopropane, 3-methyl-2-aminobutane, 1,1-dimethylaminopropane, 2-methyl-1-aminobutane, 1-methyl-1-aminobutane, 4-methyl-1-aminopentane, 3-methyl-1-aminopentane, 2-methyl-1-aminopentane, 1-methyl-1-aminopentane, 3,3-dimethyl-1-aminobutane, 2,3-dimethyl-1-aminobutane, 2,4-dimethyl-1-aminobutane, 1,2-dimethyl-1-aminobutane, 2,2dimethyl-1-aminobutane, 1,1-dimethyl-1-aminobutane, 1,1,2-trimethylaminopropane, 3-methyl-3-aminopentane, 2-ethyl-1-aminobutane, 2-heptylamine or 2-octylamine.

The cationic form of aminoalcohol derivative is preferably a cationic form of 2-ethanolamine, 2-methoxyethylamine, 3-methoxy-1-propylamine, 2-(2-aminoethoxy)-ethanol, 3-amino-1-propanol or 3-ethoxypropylamine. The cationic form of arylamine is preferably a cationic form of aniline, o-toluidine, m-toluidine, p-toluidine, 2,3-xylidine, 2,4-xylidine, 2,5-xylidine, 2,6xylidine, 3,4-xylidine, 3,5-xylidine, o-aminophenol, m-aminophenol, p-aminophenol, o-nitroaniline, m-nitroaniline, p-nitroaniline, benzidine, o-tolidine, o-phenylenediamine, m-phenylenediamine or p-phenylenediamine. The cationic form of arylalkylamine is preferably a cationic form of benzylamine or β-phenylethylamine. The cationic form of cycloalkylamine is preferably a cationic form of cyclobutylamine, cyclopentylamine, cyclohexylamine, cycloheptylamine or cyclooctylamine. The cationic form of polycycloalkylamine is preferably a cationic form of 1-aminodecalin, 2-aminodecalin, 1-aminotetralin, 2-aminotetralin, 1-adamantamine or 2-adamantanamine.

The cationic form of secondary amine is preferably a cationic form of dimethylamine, diethylamine, dipropylamine, diisopropylamine, dibutylamine, dihexylamine, diphenylamine, diethanolamine, dibenzylamine, methylethylamine, di(2-methoxyethyl) amine, ditridecylamine, N-methylaniline, N-ethylaniline, N-methylcyclohexylamine, cyclohexylamine, N-methylethanolamine or N-ethylcyclohexylamine. The cationic form of tertiary amine is preferably a cationic form of trimethylamine, triethylamine, tripropylamine, tributylamine, tripentylamine, triisopropylamine, N,N-dimethylbutyl amine, N,N-dimethylethyl amine, N,N-dimethylcyclohexylamine, N-methylcyclohexylamine, diisopropylethylamine, tris[2-(2-methoxyethoxy)ethyl] amine, N,N-dimethylaniline, 1,8-bis(dimethylamino) naphthalene, tribenzylamine, triphenylamine, N,N-dimethylethanolamine, N,N-dimethylaminodiglycol or N,N-diethylethanolamine. The cationic form of polyamine is preferably a cationic form of histamine, dopamine, isophorone diamine, polylysine, polyhistidine, 1,2-diaminocyclohexane, ethylenediamine, diethylenetriamine, triethylenetetramine, tetraethylenepentamine, polyallylamine, tetramethylethylene diamine, polyvinylpyridine, pentaethylenehexamine, N,N-bis(3- aminopropyl) methylamine, 2-(diethylamino)ethylamine, 3-(diethylamino)propylamine, 3,3'-dimethyl-4,4'-diaminodicyclohexylmethane, 3-(dimethylamino) propylamine, iminobispropylamine, 3-(methylamino) propylamine, neopentanediamine, N,N,N,N,N-pentamethyldiethylenetriamine, 1,2-propylenediamine, N,N,N',N'-tetramethyl-1,6-hexanediamine, N-(2-aminoethyl)ethanolamine, 1,6-diaminohexane-N,N,N',N'-tetraacetic acid or 4,7,10-trioxatridecane-1, 13-diamine.

The cationic form of amino acid is preferably a cationic form of a natural amino acid, an unnatural amino acid, an ester of an amino acid or an amide of an amino acid. The cationic form of natural amino acid is preferably a cationic form of L-alanine, L-cysteine, L-aspartic acid, L-glutamic acid, L-phenylalanine, glycine, L-histidine, L-isoleucine, L-lysine, L-leucine, L-methionine, L-asparagine, L-proline, L-glutamine, L-arginine, L-serine, L-threonine, L-valine, L-tryptophan, L-tyrosine, selenocysteine, β-alanine, isoglutamine, norleucine, norvaline, ornithhine, penicillamine, pyroglutamic acid, sarcosine, statine, homoserine, p-aminobenzoic acid or γ-aminobutyric acid. The cationic form of unnatural amino acid is preferably a cationic form of D-alanine, D-cysteine, D-aspartic, acid, D-glutamic acid, D-phenylalanine, D-histidine, D-isoleucine, D-lysine, D-leucine, D-methionine, D-asparagine, D-proline, D-glutamine, D-arginine, D-serine, D-threonine, D-valine, D-tryptophan, D-tyrosine, hydroxyethyl-cysteine, trans-3-methylproline, iminodiacetic acid, homoglutamine, nitroglutamine, allo-threonine, hydroxyethylhomocysteine, α,α,α-trifluoroalanine or pipecolic acid.

The cationic form of ester of an amino acid is preferably a cationic form of an alkyl ester or an aryl ester. The cationic form of alkyl ester of an amino acid is preferably a cationic form of alanine methyl ester, cysteine methyl ester, aspartic acid methyl ester, glutamic acid methyl ester, phenylalanine methyl ester, glycine methyl ester, histidine methyl ester, isoleucine methyl ester, lysine methyl ester, leucine methyl ester, methionine methyl ester, asparagine methyl ester, proline methyl ester, glutamine methyl ester, arginine methyl ester, serine methyl ester, threonine methyl ester, valine methyl ester, tryptophan methyl ester, tyrosine methyl ester, sarcosine methyl ester, iminodiacetic acid dimethyl ester, alanine ethyl ester, cysteine ethyl ester, aspartic acid ethyl ester, glutamic acid ethyl ester, phenylalanine ethyl ester, histidine ethyl ester, isoleucine ethyl ester, lysine ethyl ester, leucine ethyl ester, methionine ethyl ester, asparagine ethyl ester, proline ethyl ester, glutamine ethyl ester, arginine ethyl ester, serine ethyl ester, threonine ethyl ester, valine ethyl ester, tryptophan ethyl ester, tyrosine ethyl ester, iminodiacetic acid diethyl ester, sarcosine ethyl ester, aspartic dimethyl ester, aspartic diethyl ester, glutamic dimethyl ester or glutamic diethyl ester.

The cationic form of aryl ester of an amino acid is preferably a cationic form of alanine benzyl ester, cysteine benzyl ester, aspartic acid benzyl ester, aspartic acid dibenzyl ester, glutamic acid benzyl ester, glutamic acid dibenzyl ester, phenylalanine benzyl ester, glycine benzyl ester, histidine benzyl ester, isoleucine benzyl ester, lysine benzyl ester, leucine benzyl ester, methionine benzyl ester, asparagine benzyl ester, proline benzyl ester, glutamine benzyl ester, arginine benzyl ester, serine benzyl ester, threonine benzyl ester, valine benzyl ester, tryptophan benzyl ester, tyrosine benzyl ester or sarcosine benzyl ester. The cationic form of an amide of an amino acid is preferably a cationic form of alaninamide, cysteinamide, aspartic acid amide, aspartic acid diamide, glutamic acid amide, glutamic acid diamide, phenylalaninamide, glycinamide, histidinamide, isoleucinamide, lysinamide, leucinamide, methioninamide, asparaginamide, prolinamide, glutaminamide, argininamide, serinamide, threoninamide, valinamide, tryptophanamide, tyrosinamide, sarcosinamide or γ-aminobutyric acid amide. The cationic form of dendrimeric amine is preferably a cationic form of poly(propyleneimine) or poly-(amidoamine). The cationic form of a heterocycle is preferably a cationic form of cis-2,6-dimethylmorpholine, N,N'-dimethylpiperazine, 2,2'-dimorpholinodiethylether, N-ethylpiperidine, N-methylpiperidine, morpholine, N-methylmorpholine, 1,3,5-tris (dimethylaminopropyl)-sym-hexahydrotriazine, phenanthroline, pyrrolidine, piperidine, piperazine, quinuclidine, pyridine, 4-t-butylpyridine, 4-dimethylaminopyridine, 4-(5-nonyl) pyridine, oxazole, isoxazole, purine, 1-azabicyclo[2.2.1] heptane, carbazole, imidazole, thiazole, pyrazole, isothiazole, quinoline, isoquinoline, quinoxaline, pyridazine, pyrimidine, pyrazine, a methylpyridine, a dimethylpyridine, 2,4,6-trimethyl-pyridine, nicotinamide, nicotinic acid methyl ester, nicotinic acid ethyl ester, nicotinic acid benzyl ester or 2-chloro4-ethylamino-6-isopropylamino-1,3,5-triazine (atrazine).

The ammonium cation is preferably a cationic form of ammonium, tetramethyl ammonium, tetraethyl ammonium, tetrapropyl ammonium, tetrabutyl ammonium, tetraphenyl ammonium, paraquat, diquat, hexadecyltrimethyl ammonium, dodecyltrimethyl ammonium, octyltrimethyl ammonium, benzyldimethylhexadecyl ammonium, benzyldimethyldodecyl ammonium, benzyldimethyloctyl ammonium, cetyltrimethyl ammonium, 1-methylpyridinium, 1-ethylpyridinium, 1-hexadecylpyridinium, 1-dodecylpyridinium, 1-(1-adamantyl)pyridinium or 1-(carboxymethyl)pyridinium. The cationic form of ammonium can also be a methyl, ethyl, propyl or butyl ester of triethylammonium, tripropylammonium, tributylammonium, tripentylammonium, trihexylammonium, triheptylammonium or trioctylammonium. The hydrazine derivative cation is preferably a cationic form of hydrazine, 2,4-dinitrophenylhydrazine, hydrazinobenzoic acid, 1,1-dimethylhydrazine, 1,1-diphenylhydrazine or 1,2-diphenylhydrazine. The amidinium cation is preferably a cationic form of creatine. The sulfoxonium cation is preferably a cationic form of trimethylsulfoxonium.

The sulfonium cation is preferably a cationic form of trimethylsulfonium, diphenyl methylsulfonium, triphenylsulfonium, triethylsulfonium, diphenyl ethylsulfonium or dimethylphenacylsulfonium. The phosphonium cation is preferably a cationic form of tetramethylphosphonium, tetraethylphosphonium, tetrabutylphosphonium, tetraphenyl phosphonium, tetrakis (hydroxymethol)phosphonium or phosphazene. The cation can be guanidinium cation. The cationic form of biologically active amine is preferably a cationic form of chlorhexidine, mafenide, hexamethylpararosaniline, aminacrine, ethoxazene, phenazopyridine, amikacin, gentamicin, kanamycin, bekanamycin, neomycin, streptomycin, tobramycin, lincomycin, clindamycin, erythromycin, colistin, polymyxin B, tetracycline, chlorotetracycline, rolitetracycline, oxytetracycline, spectino-mycin, viomycin, bacampicyline, stallimycin, tromantadine, miconazole, econazole, chlormiconazole, chlormidazole, isoconazole, bifonazole, diamthazole, halethazole or hexetidine.

In a preferred embodiment, the cation is herbicidally active or compatible with the herbicidal activity of an anion with which it is associated. The cation is also preferably environmentally acceptable.

Analysis by $^{31}$P and $^{13}$C NMR techniques of the reaction products from the step of contacting phosphoric anhydride and a cyanide reveals the presence of at least the products of dicyanophosphinate salts of the formula (I), cyanopolyphosphates of the formula (II) and (III) and tricyanocyclotriphosphonate or tetracyanocyclophosphonate of the formula (IV) and (V), respectively. Addition of water and/or heating can promote the hydrolysis of dicyanophosphinate of the formula (I) to cyanophosphonate and polycyanocyclopolyphosphonates of the formula (IV) or (V). Cyanopolyphosphates of the formula (II) and (III) can be hydrolyzed to cyanophosphonate and inorganic phosphate.

The compounds produced in the above synthesis can be used as a precursors for producing other organophosphorus species. For example, those compounds can be quenched with water or a buffer to produce a cyanophosphonate derivative of cyanophosphonic acid. In a preferred embodiment, those cyanophosphonate derivatives can be hydrogenated to produce an aminomethylphosphonate derivative. The hydrogenation can take place by contacting the novel compound with hydrogen and water in the presence of a suitable catalyst under sufficient conditions to produce an aminomethylphosphonate derivative.

In a preferred embodiment, the catalyst for use in such a hydrogenation step is a transition metal catalyst. For example, the hydrogenation step can use a catalyst of a cobalt-containing compound, a nickel-containing compound, a platinum-containing compound, a palladium-containing compound or a rhodium-containing compound. More preferably, the catalyst is Raney cobalt, Raney nickel, platinum tetrachloride ($PtCl_4$) promoted Raney nickel, platinum on carbon, palladium on carbon or rhodium on carbon. The catalyst can be used at a stoichiometric amount or catalytic amount with respect to the cyanophosphonate derivative. The stoichiometric amount is preferably between about 1 molar equivalent and 5 molar equivalents with respect to the cyanophosphonate derivative, and more preferably between about 1 molar equivalent and 2 molar equivalents with respect to the cyanophosphonate derivative. The catalytic amount is preferably between about 0.1 molar percent and 100 molar percent with respect to the cyanophosphonate derivative, and more preferably between about 0.5 molar percent and about 50 molar percent with respect to the cyanophosphonate derivative.

In the event that a catalyst of platinum on carbon, palladium on carbon or rhodium on carbon is used, the hydrogenation reaction mixture preferably further contains an acid in an amount sufficient to promote formation of the desired product. The acid can be an inorganic acid or an organic acid. The inorganic acid is preferably hydrochloric acid, sulfuric acid, phosphoric acid, or nitric acid, and more preferably, hydrochloric acid. The organic acid is preferably acetic acid, trifluoroacetic acid, trifluoromethanesulfonic acid, or p-toluenesulfonic acid. The acid can be present at a concentration between about 0.1 and about 5 molar equivalents with respect to the cyanophosphonate derivative, more preferably at a concentration between about 0.5 and about 2.5 molar equivalents with respect to the cyanophosphonate derivative, and most preferably at a concentration of about 1 molar equivalent or about 2 molar equivalents with respect to the cyanophosphonate derivative, depending on the degree of protonation.

In a preferred embodiment the reaction product mixture from the hydrogenation step is heated under sufficient conditions to fhurther promote the formation of the aminomethylphosphonate derivative. For example, a product mixture that has been partially or substantially hydrogenated can be heated to a temperature in the range of about 135° C. to about 200° C., and more preferably to a range of about 135° C. to about 160° C. This heating step may be conducted for any amount of time that further promotes the aminomethylphosphonate derivative formation, preferably about 1 to about 12 hours. The heating time for optimum aminomethylphosphonate derivative formation can depend on the pH and the nature of the cations in the reaction mixture.

Further details regarding cyanophosphonate derivative hydrogenation are provided in co-pending U.S. application Ser. No. 08/996,948, entitled "Method for Preparing Aminomethylphosphonate Derivatives Via Hydrogenation of Cyanophosphonate Derivatives," by Patrick J. Lennon, filed Dec. 23, 1997, which is incorporated herein by reference.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation of Cyanopolyphosphates

This reaction was carried out in dry acetonitrile (2 mL) with $P_4O_{10}$ (0.07 g, 0.25 mmol), triethylamine (0.10 g, 1.0 mmol) and $K^{13}CN$ (0.14 g, 2.12 mmol) with stirring under reflux for 72 hours. The solvent and amine were removed under reduced pressure. The solid residue was hydrolyzed with $D_2O$ yielding 36% of cyanophosphonate derivatives: 21% as cyanophosphonate at −14.6 ppm (doublet) and 16% as compounds with chemical shifts from −31.2 to −34.5 ppm (sets of multiplets), 62% linked polyphosphate groups with chemical shift at range −19.5 to −23.8 ppm in the $^{31}$P NMR spectrum, and 2% tripolyphosphate. Two dimensional $^{31}$P NMR techniques show that a triplet at −23.7 ppm (J=20.7 Hz) and a doublet of doublets at −33.3 ppm ($^1J_{P-C}$=199.2 Hz, $^2J_{P-P}$=20.3 Hz) are coupled. Other significant PCN species include: −4.1 (doublet, J =−22.8 Hz), coupled to a peak at −30.67 (doublet of doublets, J=188.1 Hz, 22.3 Hz) which appears to be monocyanopyrophosphate; a large doublet of doublets at −32.68 (J=198.2, 19.1 Hz) coupled to a multiplet at −22 to −23. Other large multiplets observed in the region −32 to −34 ppm.

Example 2

Preparation of Dicyanophosphinate

The reaction was carried out in acetonitrile (1 mL) with $P_4O_{10}$ (0.07 g, 0.25 mmol), triethylamine (0.04 g, 0.4 mmol), and $K^{13}CN$ (0.04 g, 0.61 mmol) at 50° C. for 16 hours. The acetonitrile solution containing the soluble components was separated from the precipitate. The $^{31}$P and $^{13}$C NMR spectra show the presence of dicyanophosphinate ion and triethylamine: $^{31}$P NMR ($CH_3CN$) δ (ppm) −52.4 (triplet, $^1J_{P-C}$=152.6 Hz), $^{13}$C NMR ($CH_3CN$) δ (ppm) 121.0 (doublet, $^1J_{C-P}$=152.6 Hz), and two weak signals at 45 and 9.5 ppm attributable to triethylamine.

Example 3

Preparation of Tricyanocyclotriphosphonate or Tetracyanocyclotetraphosphonate and Cyanophosphonate from Dicyanophosphinate The volatile components from the solution of Example 2 were removed under reduced pressure. The resulting solid residue was hydrolyzed with $D_2O$ yielding tricyanocyclotriphosphonate or tetracyanocyclotetraphosphonate (65%): $^{31}P$ NMR ($D_2O$) δ (ppm) −34.0 (doublet of triplets, $^1J_{P-C}$= 204.5 Hz, $^3J_{P-C}$=10.7 Hz), $^{13}C$ NMR ($D_2O$) δ (ppm) 118.5 (doublet, $^1J_{C-P}$=202.4 Hz); and cyanophosphonate (35%): $^{31}P$ NMR ($D_2O$) δ (ppm) −19.0 (doublet, $^1J_{P-C}$=174.0 Hz), $^{13}C$ NMR ($D_2O$) δ (ppm) 120.6 (doublet, $^1J_{C-P}$=174.9 Hz). Yields represent relative amounts of phosphorus species in solution, and not absolute yields.

Example 4

Preparation of Cyanophosphonate from Dicyanophosphinate via Tricyanocyclotriphosphonate or tetracyanocyclotetraphosphonate The reaction was carried out in dry acetonitrile (1 mL) with $P_4O_{10}$ (0.07 g, 0.25 mmol), triethylamine (0.056 g, 0.55 mmol), and potassium cyanide (0.05 g, 0.77 mmol) at 50° C. for 4 hours. The acetonitrile solution containing the soluble components was separated from the precipitate. The $^{31}P$ NMR spectrum of this solution shows the presence of dicyanophosphinate: $^{31}P$ NMR ($CH_3CN$) δ (ppm) −52.5 (singlet). The volatile components were removed under reduced pressure. The solid residue obtained was hydrolyzed in $D_2O$ yielding 27% of tricyanocyclotriphosphonate or tetracyanocyclotetraphosphonate: $^{31}P$ NMR ($D_2O$) δ (ppm) −34.0; and 73% of cyanophosphonate: $^{31}P$ NMR ($D_2O$) δ (ppm) −20.3. After heating to 50° C. for 2 days, polycyanocyclopolyphosphonate was completely transformed into cyanophosphonate, as evidenced by $^{31}P$ NMR spectra. The identity of cyanophosphonate was confirmed by addition of disodium cyanophosphonate to the studied solution and recording the $^{31}P$ NMR spectrum for the combined samples: only one signal was observed, with a chemical shift of −18 ppm. Yields represent relative amounts of phosphorus species in solution, and not absolute yields.

Example 5

Preparation of Tricyanocyclotriphosphonate or Tetracyanocyclotetraphosphonate and Conversion to Cyanophosphonate This reaction was carried out in dry acetonitrile (1 mL) with $P_4O_{10}$ (0.07 g, 0.25 mmol), triethylamine (0.10 g, 1.0 mmol), and $K^{13}CN$ (0.07 g, 1 mmol) at 80° C. for 120 hours. The soluble components were separated from the precipitate. The $^{31}P$ NMR spectrum shows the presence of tricyanocyclotriphosphonate or tetracyanocyclotetraphosphonate: $^{31}P$ NMR ($D_2O$) δ (ppm) −35.5 (doublet of triplets, $^1J_{P-C}$=155.6 Hz, $^3J_{P-C}$=12.2 Hz). The volatile fractions were removed. The solid residue obtained was dissolved in $D_2O$ (1 mL) with traces of potassium hydroxide (pH=9.0) yielding 71% of tricyanocyclotriphosphonate or tetracyanocyclotetraphosphonate: $^{31}P$ NMR ($D_2O$) δ (ppm) −34.0 (apparent doublet of triplets, $^1J_{P-C}$=201.4 Hz, $^3J_{P-C}$=10.7 and 12.21 Hz), $^{13}C$ NMR ($D_2O$) δ (ppm) 120.6 (doublet, $^1J_{C-P}$=144.3 Hz). Yields represent relative amounts of phosphorus species in solution, and not absolute yields.

Example 6

Preparation of Cyanophosphonate Derivatives from Phosphoric Anhydride and Cyanides for NMR Analysis Preparation 1.

Under inert atmosphere, 0.07 g (0.25 mol) of $P_4O_{10}$ was mixed with 1 ml of dry $CH_3CN$ and 0.10 g (1.0 mmol) of triethylamine were added. The mixture was then heated at 40° C. for 5 minutes, after that 0.07 g (1.06 mmol) of KCN were added to this solution. The solid KCN was crushed with a spatula around the walls of the glass vial under the surface of the reaction mixture. The mixture was heated at 40° C. overnight. After removal of the solvent under reduced pressure, the resulting powder was dissolved in $D_2O$ and the NMR spectra were recorded. The pH was adjusted as needed by the addition of acid or base.

Preparation 1a.

The reaction was carried out according to the procedure in Example 1 using the same molar quantities of reagents, except that $K^{13}CN$ was used instead of $K^{12}CN$.

Preparation 2.

Under inert atmosphere, 0.07 g (0.25 mol) of $P_4O_{10}$ was mixed with 1 ml of dry $CH_3CN$ and 0.135 g (1.0 mmol) of 4-tert-butylpyridine were added. The mixture was then heated at 40° C. for 5 minutes, after that 0.07 g (1.06 mmol) of KCN were added to this solution. The solid KCN was crushed with a spatula around the walls of the glass vial under the surface of the reaction mixture. The mixture was heated at 40° C. overnight. After removal of the solvent under reduced pressure, the resulting powder was dissolved in $D_2O$ and the NMR spectra were recorded. The pH was adjusted as needed by the addition of acid or base.

Preparation 3.

Under inert atmosphere, 0.07 g (0.25 mol) of $P_4O_{10}$ was mixed with 1 ml of dry $CH_3CN$ and 0.10 g (1.0 mmol) of triethylamine were added. The mixture was then heated at 40° C. for 5 minutes, after that 0.269 g (1.0 mmol) of $(C_4H_9)_4NCN$ were added to this solution. The mixture was heated at 40° C. overnight. A small quantity of dry $CD_3CN$ was added to the solution before the NMR spectra were run.

The product mixtures for Preparations 1, 1a, 2 and 3 were then evaluated by NMR, the results of which are summarized in Tables I–VI. The NMR experiments were carried out at a field strength of 14.1 Tesla at 25° C. Solutions of reaction mixtures prior to hydrolysis contained added $CD_3CN$ (10% v/v) and after hydrolysis were in $D_2O$. Techniques used were quantitative one dimensional $^{13}C$ and $^{31}P$ NMR, COSY (coherent spectroscopy) and TOSCY (total coherent spectroscopy).

| | Species Assignment Key for Tables I–IV, VI | |
|---|---|---|
| Molecule ID | Assignment | Formula |
| A | Cyclic trimer or tetramer | $(CN)_3(PO_2)_3$ or $(CN)_4(PO_2)_4$ |
| B | Symmetrical linear trimer | $[NCPO_3PO_3PO_2CN]^{3-}$ |
| C | Symmetrical linear tetramer | $[NCPO_3PO_3PO_3PO_2CN]^{4-}$ |
| D | Unsymmetrical linear tetramer | $[NCPO_3PO_3PO_3PO_3]^{5-}$ |

-continued

Species Assignment Key for Tables I–IV, VI

| Molecule ID | Assignment | Formula |
|---|---|---|
| E | Unsymmetrical linear pentamer | $[NCPO_3PO_3PO_3PO_3PO_3]^{6-}$ |
| L | Cyanophosphonate (monomer A) | $[NCPO_3]^{2-}$ |

Table V

| 1 | Dicyanophosphinate (monomer B) | $[(NC)_2PO_2]^{1-}$ |
| 12 | Cyclic trimer or tetramer | $(CN)_3(PO_2)_3$ or $(CN)_4(PO_2)_4$ |

TABLE I $^{31}P$ NMR Data for Preparation 1 (pH ~2.5, 3 day solution)

| Molecule ID | Approx. % | Highest Field Pattern Chemical Shift (ppm) $J_{pp}$ (Hz) | Coupled Partner Pattern Chemical Shift (ppm) $J_{pp}$ (Hz) | | | |
|---|---|---|---|---|---|---|
| A | 25.3 | S<br>−33.69 | | | | |
| B | 10.0 | D<br>−33.02<br>20.9 | T<br>−23.63<br>20.9 | | | |
| C | 3.9 | HOP<br>−32.6 | HOP<br>−22.9 | | | |
| D | 3.4 | D<br>−32.42<br>18.9 | DD<br>−22.43<br>18.8 | HOP<br>−22.27 | HOP<br>−21.77 | |
| E | 9.5 | D<br>−32.38<br>19.3 | DD<br>−22.21<br>19.2, 16.8 | DD<br>−21.56 | HOP<br>−21.1 aprox | HOP<br>−20.9 aprox |
| F | <1 | D<br>−32.17<br>20.9 | D<br>−9.83<br>20.7 | | | |
| G | <1 | D<br>−31.54<br>12.3 | partner not located | | | |
| H | 2.1 | S<br>−22.36 | | | | |
| I | <1 | S<br>−22.51 | | | | |
| J | 3.2 | D<br>−21.37<br>15.3 | O<br>−9.49<br>O | | | |
| K | 6.2 | S<br>−20.25 | | | | |
| L | 35.6 | S<br>−14.38 | | | | |
| M | <1 | S<br>−1.13 | | | | |

S = singlet
D = doublets
T = triplet
DD = doublet of doublets
HOP = higher order pattern
O = obscured

TABLE II $^{31}P$ NMR Data for Preparation 1 (pH = 8.2, 1 hr solution)

| Molecule ID | Approx. % | Highest Field Pattern Chemical Shift (ppm) $J_{p-p}$ (Hz) | Coupled Partner Pattern Chemical Shift (ppm) $J_{pp}$ (Hz) |
|---|---|---|---|
| A | 28.9 | S<br>−33.64 | |
| B | 12.4 | D<br>−33.90<br>20.9 | T<br>−23.50<br>20.9 |
| C | 4.9 | HOP<br>−32.47 | HOP<br>−22.73 |

TABLE II-continued $^{31}$P NMR Data for Preparation 1 (pH = 8.2, 1 hr solution)

| Molecule ID | Approx. % | Highest Field Pattern Chemical Shift (ppm) $J_{p-p}$ (Hz) | Coupled Partner Pattern Chemical Shift (ppm) $J_{pp}$ (Hz) | | | |
|---|---|---|---|---|---|---|
| D | 3.8 | D −32.31 18.7 | DD −22.27 18.3 | HOP −21.09 | | |
| E | 11.7 | D −32.27 19.3 | DD −22.05 19.1, 16.9 | DD −21.39 16.3, 15.3 | HOP −20 74 | HOP −20.74 |
| $^a$X | <1 | D −3 1 .50 12.90 | TOSCY sw did not include coupled portion | | | |
| $^a$Y | <1 | D −30.53 22.66 | TOSCY sw did not include coupled portion | | | |
| H | 1.1 | S −22.44 | | | | |
| I | 1.2 | S −22.21 | | | | |
| J | 7.6 | D −21.20 14.8 | TOSCY sw did not include coupled portion | | | |
| K | 26.5 | S −20.14 | | | | |
| L | | S −14.25 | | | | |

S = singlet
D = doublet
T = triplet
HOP = higher order pattern
DD = doublet of doublets
SW = sweep width
$^a$X and Y may be identical to F and G (Table I) but shifts are notably different.

TABLE III $^{31}$P NMR Data for Preparation 2 (pH = 3.2, 24 hr solution)

| Molecule ID | Approx. % | Highest Field Pattern Chemical Shift (ppm) $J_{p-p}$ (Hz) | Coupled Partner Pattern Chemical Shift (ppm) $J_{pp}$ (Hz) | | | |
|---|---|---|---|---|---|---|
| A | 39.2 | S −33.75 | | | | |
| B | 6.6 | D −33.05 20.9 | T −23.66 20.9 | | | |
| C | 2.5 | HOP −32.64 | HOP −22.92 | | | |
| D | <1 | D −32.47 19.3 | DD −22.24 | HOP −21.28 | HOP −21.78 | |
| E | 6.0 | D −32.43 19.3 | DD 22.24 | DD −21.60 | HOP −21.16 | HOP −20.95 |
| F | 9.5 | D −32.19 21.1 | −9.81 21.1 | | | |
| G | | Absent | | | | |
| H | <1 | S −22.65 | | | | |
| I | 1.4 | S −22.39 | | | | |
| J | 2.6 | D −21.46 | O −9.46 | | | |
| K | 5.4 | S −20.30 | | | | |
| L | 23.4 | S −15.67 | | | | |

TABLE III-continued $^{31}$P NMR Data for Preparation 2 (pH = 3.2, 24 hr solution)

| Molecule ID | Approx. % | Highest Field Pattern Chemical Shift (ppm) $J_{p-p}$ (Hz) | Coupled Partner Pattern Chemical Shift (ppm) $J_{pp}$ (Hz) |
|---|---|---|---|
| M | 1.0 | S +1.13 | |
| N | <1 | S −21.82 | |

S = singlet
D = doublet
T = triplet
DD = doublet of doublets
O = obscured
HOP = higher order pattern

TABLE IV $^{31}$P-$^{13}$C Coupling Constants from Preparation 1a

| Molecule ID | $J_{P-C}$ coupling constant in hertz | |
|---|---|---|
| A | $^1J_{PC}$ = 204.7 Hz | $^3J_{PC}$ = 11.04 Hz |
| B | 200.5 Hz | |
| C | 199.9 Hz | |
| D | 199.2 Hz | |
| E | 198.9 Hz | |
| L | 157.3 Hz | |

TABLE V

Chemical shifts and coupling constants for P containing molecular species in Preparation 3

| Molecule ID | Approx % | Pattern Chem Shift (ppm) $J_{p-p}$ (Hz) | Coupled Partner(s) |
|---|---|---|---|
| 1 | 16.8 | S −47.36 | |
| 2 | <1 | T −37.68 24.5 | peak at −19.47 observed by #18 |
| 3 | <1 | Q −34.90 22.7 | #7 |
| 4 | <1 | S −33.62 | |
| 5 | <1 | S −33.44 | |
| 6 | <1 | DX −32.92 25.88 | 6A |
| 7 | 2.1 | S −32.75 23 | #3 |
| 8 | 1.7 | M −32.55 | 15, 16 |
| 9 | <1 | D −21.82 | CNL |
| 10 | <1 | D −32.18 | CNL |
| 11 | 7.2 | D −31.8 19.1 | 13, 18 |
| 12 | 9.2 | S −30.9 | |
| 13 | 7.3 | HOP 29.86 | 11, 18 |
| 14 | 20.4 | D −29.71 20.6 | 17 |
| 15 | 1.4 | HOP −22,32 | 8, 16 |
| 16 | <1 | T −21.48 24.0 | 15, 8 |
| 17 | 10 | T −20.28 21.05 | 14 |
| 18 | 16 | D −19.54 | 11, 13 |
| 19 | 3 | D −19.08 22.5 | obscured peak at 30.2 ppm |
| 20 | <1 | D −18.11 22.5 | obscured peak at 29.5 |
| 6A | <1 | D −31.17 25.88 | 6 |

S = singlet
D = doublet
T = triplet
Q = quartet
HOP = higher order pattern
CNL = cannot locate

TABLE VI $^{13}$C Chemical Shifts and C-P Coupling Constants for CN Containing Species in Preparation 1a with Triethylamine Base (5 day solution)

| Molecule ID | Approx. % | $^{13}$C Chemical Shift$^a$ (ppm) | $^1J_{CP}$ Hz | $^3J_{CP}$ Hz |
|---|---|---|---|---|
| A | 12.3 | 116.34 | 204.7 | 11.0 |
| B | 7.1 | 116.80 | 200.5 | |
| C | 3.8 | 117.01 | 199.9 | |
| D | 2.9 | 117.09 | 199.2 | |
| E | 5.5 | 117.10 | 198.9 | |
| $^b$F | 1.2 | 117.10 | 196.2 | |
| $^b$G | <1 | 117.40 | 174.4 | |

TABLE VI-continued $^{13}$C Chemical Shifts and C-P Coupling Constants for CN Containing Species in Preparation 1a with Triethylamine Base (5 day solution)

| Molecule ID | Approx. % | $^{13}$C Chemical Shift[a] (ppm) | $^1J_{CP}$ Hz | $^3J_{CP}$ Hz |
|---|---|---|---|---|
| L | 35.0 | 119.71 | [c]166.7 | |
| O | 31.6 | 110.80 | | |

[a]referenced to $CH_3CN$ at 118.2 ppm
[b]assignment speculative
[c]this $^1J_{CP}$ is time dependent

Example 7

Preparation of Phosphonitrile Derivatives from Phosphoric Anhydride and Hydrocyanic Acid As a general example, under an inert atmosphere, 1 molar part of $P_4O_{10}$ was mixed with a dry polar solvent ($CH_3CN$ is preferred, 4 mL per mmol $P_4O_{10}$) and a few molar parts (four parts are preferable) of a dry aprotic base were added. The mixture was then heated at 30–40° C. to effect partial or total dissolution of $P_4O_{10}$ (about 5 to 10 minutes), after which several molar parts (four parts are preferable) of dry liquid $H^{12}CN$ or $H^{13}CN$ or a mixture of both were added to this solution cooled in an ice bath with magnetic stirring. The mixture was heated at the specified temperature, usually between 30 and 80° C., for the specified time period, often between 2 and 20 hours. At the end of this time period, the solution was purged by nitrogen for 2 hours to remove free HCN. The rest of the volatile compounds were removed using a vacuum pump then the viscous residue was hydrolyzed by water or buffer. The yield of cyanophosphonate derivatives was analyzed before and after hydrolysis.

In a particular example, the reaction was carried out in 8 ml of $CH_3CN$ with $P_4O_{10}$ (0.56 g, 1.97 mmol), quinuclidine (0.89 g, 8.0 mmol) and $H^{13}CN$ (0.4 mL, 10 mmol) at 48° C. for 16 hours, giving a homogeneous solution. After purging with nitrogen, $^{31}P$ NMR showed the presence of 87.6% of P-CN containing species (major signals correspond to cyclic tricyanotripolyphosphonate: $^{31}P$ NMR ($CH_3CN$) −35 ppm (dt, $^1J_{PC}$=187.7 Hz, $^3J_{PC}$=11.0 Hz), $^{13}C$ NMR ($CH_3CN$) 120.3 ppm (doublet of triplets, $^1J_{CP}$32 187.2 Hz, $^3J_{CP}$=11.0 Hz) and dicyanotripolyphosphate $^{31}P$ NMR ($CH_3CN$) −34.5 ppm (dd, $^1J_{PC}$=184.6 Hz, $^3J_{PP}$=19.8 Hz), $^{13}C$ NMR ($CH_3CN$) 121.3 ppm (dd, $^1J_{CP}$=184.4 Hz, $^3J_{CP}$=2.0 Hz). Part of the $CH_3CN$ solution was hydrolyzed in water (4:1, $CH_3CN:H_2O$) yielding the same ratio of products. The solvent of another portion of unhydrolyzed reaction mixture was removed under reduced pressure. A portion of this solid, 0.1 g, was hydrolyzed in 1 mL of buffer at pH=2 (final pH of medium, 5.0), giving 87.2% of P-CN containing species (cyclic tricyanotripolyphosphonate: $^{31}P$ NMR ($H_2O$) −34 ppm (dt, $^1J_{PC}$=202.9 Hz, $^3J_{PC}$=11.0 Hz), $^{13}C$ NMR ($H_2O$) 117.2 ppm (dt, $^1J_{CP}$=201.8 Hz, $^3J_{CP}$=11.0 Hz) and dicyanotripolyphosphate $^{31}P$ NMR ($H_2O$) −33.2 ppm (dd, $^1J_{PC}$=198.4 Hz, $^3J_{PP}$=21.4 Hz), $^{13}C$ NMR ($H_2O$) 117.6 ppm ($^1J_{CP}$=198.4 Hz).

Additional representative conditions and yields are shown in Table VII.

TABLE VII

Reactions of HCN and $P_4O_{10}$

| mmol of HCN | mmol of $P_4O_{10}$ | Additive (mmol) | Temp ° C. | Time | Solvent | Yield P-CN (%) before hydrolysis | Yield P-CN (%) after hydrolysis (final pH or solvent) |
|---|---|---|---|---|---|---|---|
| 12.95 | 3.0 | $NEt_3$ (12) | 40 | 16 h | $CH_3CN$ | 62 | 60 (pH = 3.0) |
| | | | | | | | 51 (pH = 9.0) |
| | | | 40 | 7 d | $CH_3CN$ | 66 | 62 (pH = 3.0) |
| 12.95 | 3.17 | 4-t-BuPy (12.6) | 40 | 18 h | $CH_3CN$ | 63 | 36 (pH = 3.0) |
| | | | | | | | 47 (pH = 6.0) |
| 15.5 | 1.50 | 4-t-BuPy (6.0) | 70 + 40 | 1 + 16 h | $CH_3CN$ | 40 | 22 (pH = 7.0) |
| 5.18 | 0.50 | none | 40 | 16 h | $CH_3CN$ | 0 | 0 |
| 12.95 | 3.0 | $NEt_3$ (2.0) | 50 | 48 h | $C_6H_5CN$ | 0 | 0 |
| 46.6 | 0.5 | none | 34 | 20 h | none | 0 | 0 |
| 15.6 | 3.0 | TMED (12.0) | 80 | 16 h | $CH_3CN$ | 72 | 68.2 (in $CH_3CN$) |
| | | | | | | | 28.6 (pH = 1.0) |
| 15.6 | 3.0 | TMBD (12.0) + $NEt_3$(12.0) | 70 + 40 | 1 + 16 h | $CH_3CN$ | 64.6 | 62.1 (in $CH_3CN$) |
| 15.6 | 3.0 | Proton-Sponge (11.7) | 80 | 16 h | $CH_3CN$ | 67 | 48.7 (in $CH_3CN$) |
| 14.26 | 2.47 | TBBD (8.84) | 45 | 16 h | $CH_3CN$ | 55.7 | 51.0 (in $CH_3CN$) |
| 10.37 | 3.24 | DBU (10.0) | 80 | 16 h | $CH_3CN$ | 41.8 | 41.2 (in$CH_3CN$) |
| 9.07 | 1.80 | Quinuclidine (7.1) | 48 | 16 h | $CH_3CN$ | 84.9 | 84.7 (in $CH_3CN$) |
| | | | | | | | 79.1 (pH = 6.0) |
| 11.7 | 2.22 | $NBu_3$ (9.12) | 40 | 64 h | $CH_3CN$ | 68.3 | 61.6 (in $CH_3CN$) |
| 17.5 | 2.22 | Quinuclidine (8.02) | 48 | 16 h | $CH_3CN$ | 82.2 | 75.4 (in $CH_3CN$) |
| 10.0 | 1.97 | Quinuclidine (8.0) | 48 | 16 h | $CH_3CN$ | 87.6 | 87.6 (in $CH_3CN$) |
| | | | | | | | 87.2 (pH = 5) |

$NEt_3$ is triethyl amine.
4-t-BuPy is 4-tert-butylpyridine.
TMED is N,N,N',N'-tetramethylethylenediamine.
Proton sponge ® is 1,8-bis(dimethylamino)naphthalene.
TEED is N,N,N',N'-tetraethylethylenediamine.
DBU is 1,8-diazabicyclo[5.4.0]undec-7-ene.
$NBu_3$ is tri-n-butylamine.

While the compositions and methods of this invention have been described in terms of preferred embodiments, in light of this patent disclosure it will be apparent to those of skill in the art that variations can be applied to the process described herein without departing from the concept, spirit and scope of the invention. All such similar substitutes and modifications apparent to those skilled in the art are deemed to be within the spirit, scope and concept of the invention.

What is claimed is:

1. A compound of the formula (II) or (III):

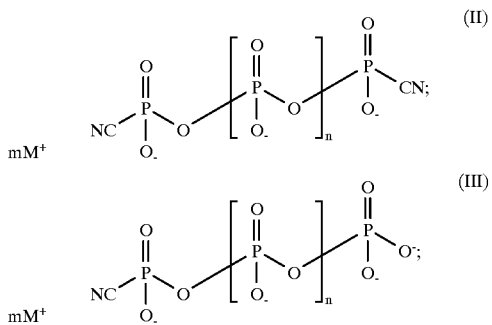

wherein $M^+$ is one or more suitable monovalent or polyvalent cations, m is the number of $M^+$ cations and n is an integer.

2. The compound of claim 1, wherein $M^+$ comprises a hydrogen cation, an alkali metal cation, an alkaline earth metal cation, a transition metal cation, a group III metal cation, a lanthanide cation, an actinide cation, a cationic form of a primary amine, a cationic form of a secondary amine, a cationic form of a tertiary amine, a cationic form of a polyamine, a cationic form of an amino acid, a cationic form of a dendrimeric amine, a cationic form of a heterocycle, an ammonium cation, a quarternary ammonium cation, a cationic hydrazine derivative, an amidinium cation, a sulfoxonium cation, a sulfonium cation, a phosphonium cation, a guanidinium cation, hydrogen, a cationic form of a biologically active amine or mixtures thereof.

3. The compound of claim 2, wherein $M^+$ is an alkali metal cation.

4. The compound of claim 3, wherein $M^+$ is a lithium cation, a sodium cation or a potassium cation.

5. The compound of claim 2, wherein $M^+$ is an ammonium cation.

6. The compound of claim 5, wherein $M^+$ is an ammonium derivative.

7. The compound of claim 6, wherein $M^+$ is an isopropylammonium cation.

8. The compound of claim 6, wherein $M^+$ is an dimethylammonium cation.

9. The compound of claim 6, wherein $M^+$ is a 2-hydroxyethylammonium cation.

10. The compound of claim 6, wherein $M^+$ is a triethylammonium cation.

11. The compound of claim 6, wherein $M^+$ is a trimethylammonium cation.

12. The compound of claim 6, wherein $M^+$ is a tetramethylammonium cation.

13. The compound of claim 6, wherein $M^+$ is a tetrabutylammonium cation.

14. The compound of claim 2, wherein $M^+$ is a sulfonium cation.

15. The compound of claim 14, wherein $M^+$ is a trimethyl sulfonium cation.

16. The compound of claim 2, wherein $M^+$ is a phosphonium cation.

17. The compound of claim 16, wherein $M^+$ is a tetramethylphosphonium cation.

18. The compound of claim 2, wherein $M^+$ is a sulfoxonium cation.

19. The compound of claim 18, wherein $M^+$ is a trimethylsulfoxonium cation.

20. The compound of claim 1, wherein the cation is herbicidally active.

21. The compound of claim 1, wherein the compound is of formula (II) or (III) and n is an integer from 0 to 10.

22. The compound of claim 21, wherein the compound is of formula (II) or (III) and n is an integer from 0 to 5.

23. The compound of claim 22, wherein the compound is of formula (II) or (III) and n is an integer from 0 to 2.

24. The cyclic compound of the formula:

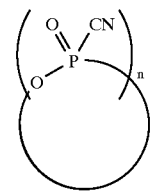

wherein n is 3 to 8.

25. A compound of claim 16, wherein the compound is of the formula (IV) or (V):

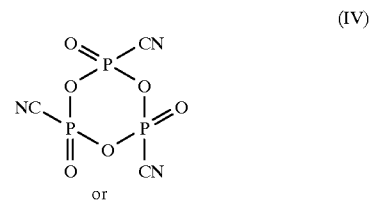

or

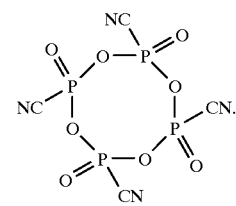

26. A process for preparing a cyanophosphonate compound of the formula (I):

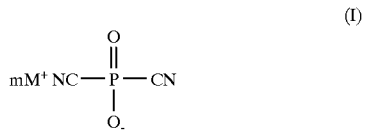

wherein $M^+$ comprises a suitable monovalent or polyvalent cation and m is the number of $M^+$ cations;

comprising contacting phosphoric anhydride and a cyanide, where the cyanide is selected from hydrogen cyanide and a cyanide salt in a reaction mixture under sufficient conditions to produce the cyanophosphate compound.

27. The process of claim 26, wherein the cyanide is hydrogen cyanide, an alkali metal cyanide, an alkaline earth metal cyanide, an ammonium cyanide, a tetraalkyl ammonium cyanide, a tetraalkyl phosphonium cyanide, a trialkyl sulfonium cyanide, a cyanide of a cationic form of an organic amine or mixtures thereof.

28. The process of claim 27, wherein the cyanide is hydrogen cyanide, potassium cyanide, sodium cyanide, lithium cyanide, tetrabutylammonium cyanide or mixtures thereof.

29. The process of claim 26, wherein the molar ratio of the cyanide to phosphoric anhydride added to the reaction mixture is from about 1 to about 15.

30. The process of claim 29, wherein the molar ratio of the cyanide to phosphoric anhydride added to the reaction mixture is in the range of about 2 to about 10.

31. The process of claim 30, wherein the molar ratio of the cyanide to phosphoric anhydride added to the reaction mixture is in the range of about 3.5 to about 8.5.

32. The process of claim 26, wherein the temperature of the reaction mixture during the contacting step is in the range of about −20° C. to about 150° C.

33. The process of claim 32, wherein the temperature of the reaction mixture during the contacting step is in the range of about 30 to about 90° C.

34. The process of claim 26, wherein the reaction time ranges from about 0.1 to about 50 hours.

35. The process of claim 34, wherein the reaction time ranges from about 0.5 to about 20 hours.

36. The process of claim 35, wherein the reaction time ranges from about 1 to about 6 hours.

37. The process of claim 26, wherein the reaction mixture further contains a solvent.

38. The process of claim 37, wherein the solvent is a polar solvent.

39. The process of claim 38, wherein the solvent is acetonitrile, benzonitrile, adiponitrile, propionitrile, dimethylacetonitrile, benzyl cyanide, sulfolane or mixtures thereof.

40. The process of claim 39, wherein the solvent is acetonitrile, benzyl cyanide or adiponitrile.

41. The process of claim 26, wherein the reaction mixture further comprises a Lewis base.

42. The process of claim 41, wherein the Lewis base is triethylamine, diglyme, 4-isopropylpyridine, 4-dimethylaminopyridine, tris[2-(2-methoxyethoxy)ethyl] amine, 4-tert-butylpyridine, 4-(5-nonyl)pyridine, trimethylamine, 1,8-bis(dimethylamino) naphthalene, 4-ethylpyridine, phenanthroline, piperidine, N,N,N,N-tetramethyl ethylenediamine, 1,4,7,10,13-pentamethyl-1,4,7,10,13-pentaazacyclopentadecane, quinuclidine, N-methylpyrrolidine, 1,4-diazobicyclo[2.2.2] octane, 1-butylimidazole, 3-benzylpyridine, 1,5-pentamethylenetetrazole, tris[2(2-methoxyethoxy)ethyl] amine, N,N-dimethylaniline, collidine, N-benzylidine aniline, triphenylphosphine or mixtures thereof.

43. The process of claim 42, wherein the Lewis base is 4-t-butylpyridine, 4-(5-nonyl)pyridine, quinuclidine or N-methylpyrrolidine.

44. The process of claim 41, wherein the molar ratio of Lewis base to phosphoric anhydride added to the reaction mixture is in the range of 1 to 10.

45. The process of claim 44, wherein the molar ratio of Lewis base to phosphoric anhydride added to the reaction mixture is in the range of 2 to 8.

46. The process of claim 45, wherein the molar ratio of Lewis base to phosphoric anhydride added to the reaction mixture is in the range of 3 to 6.

47. A compound of the formula (I):

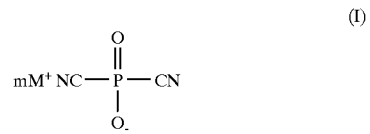

wherein $M^+$ is one or more suitable monovalent or polyvalent cations selected from the group consisting of a hydrogen cation, an alkaline earth metal cation, a transition metal cation, a group III metal cation, a lanthanide cation, an actinide cation, a cationic form of a primary amine, a cationic form of a secondary amine, a cationic form of a tertiary amine, a cationic form of a polyamine, a cationic form of an amino acid, a cationic form of a dendrimeric amine, a cationic form of a heterocycle, an ammonium cation, a quarternary ammonium cation, a cationic hydrazine derivative, an amidinium cation, a sulfoxonium cation, a sulfonium cation, a phosphonium cation, a guanidinium cation, hydrogen, a cationic form of a biologically active amine and mixtures thereon, and m is the number of $M^+$ cation.

48. A process for preparing at least one cyanophosphonate compound of the formula (II) or (III):

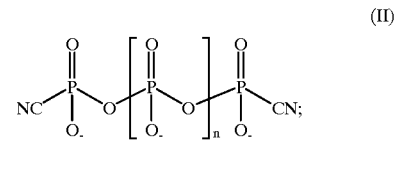

wherein $M^+$ is one or more suitable monovalent or polyvalent cations, m is the number of $M^+$ cations and n is an integer;

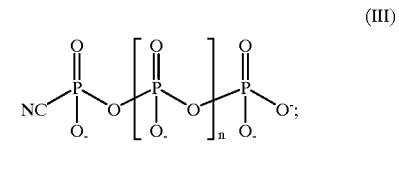

wherein $M^+$ is one or more suitable monovalent or polyvalent cations, m is the number of $M^+$ cations and n is an integer;

comprising contacting phosphoric anhydride and hydrogen cyanide or a cyanide salt in a reaction mixture under sufficient conditions to produce at least one cyanophosphate compound, wherein the reaction mixture contains a solvent selected from the group consisting of benzyl cyanide and sulfolane.

49. A process for preparing at least one cyanophosphonate compound of the formula (II) or (III):

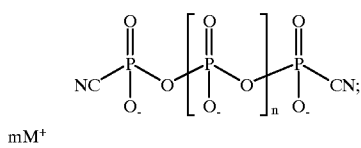

(II)

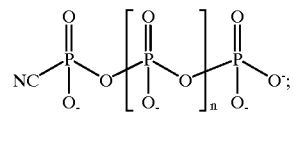

(III)

wherein $M^+$ is one or more suitable monovalent or polyvalent cations, m is the number of $M^+$ cations and n is an integer;

wherein $M^+$ is one or more suitable monovalent or polyvalent cations, m is the number of $M^+$ cations and n is an integer;

comprising contacting phosphoric anhydride and hydrogen cyanide or a cyanide salt in a reaction mixture under sufficient conditions to produce at least one cyanophosphate compound, wherein the reaction mixture contains a Lewis base selected from the group consisting of 4-isopropylpyridine and piperidine.

* * * * *